(12) United States Patent
Ye et al.

(10) Patent No.: US 8,488,850 B2
(45) Date of Patent: Jul. 16, 2013

(54) ISOTROPIC RESOLUTION IMAGE RECONSTRUCTION

(75) Inventors: Jinghan Ye, Fremont, CA (US); Xiyun Song, Santa Clara, CA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 793 days.

(21) Appl. No.: 12/594,512

(22) PCT Filed: Mar. 26, 2008

(86) PCT No.: PCT/IB2008/051133
§ 371 (c)(1), (2), (4) Date: Feb. 24, 2010

(87) PCT Pub. No.: WO2008/122903
PCT Pub. Date: Oct. 16, 2008

(65) Prior Publication Data
US 2010/0183203 A1    Jul. 22, 2010

Related U.S. Application Data

(60) Provisional application No. 60/910,037, filed on Apr. 4, 2007.

(51) Int. Cl.
*G06K 9/00* (2006.01)
(52) U.S. Cl.
USPC .................................................. 382/128
(58) Field of Classification Search
USPC .................................................. 382/128
See application file for complete search history.

(56) References Cited

U.S. PATENT DOCUMENTS

| 5,532,490 A | 7/1996 | Gullberg et al. |
| 7,158,823 B2 | 1/2007 | Hawkins |
| 2006/0078082 A1 | 4/2006 | Motomura et al. |
| 2006/0108532 A1 | 5/2006 | Ohana et al. |

FOREIGN PATENT DOCUMENTS

| JP | 57069268 A | 4/1982 |
| JP | 04036684 A | 2/1992 |
| WO | 9742592 | 11/1997 |
| WO | 2004113951 A2 | 12/2004 |
| WO | WO 2004/113951 A2 * | 12/2004 |

OTHER PUBLICATIONS

Franquiz, et al., A multiresolution restoration method for cardiac SPECT imaging, Medical Physics, Dec. 1998, pp. 2469-2475, vol. 25, No. 12, Am. Assoc. Phys. Med.

Bouwens, et al., Resolution recovery for list-mode reconstruction in SPECT, SPIE Medical Imaging 2001: Image Processing, 2001, pp. 40-51, vol. 4322.

Vandenberghe, et al., Iterative reconstruction algorithms in nuclear medicine, Computerized Medical Imaging and Graphics, 2001, pp. 105-111, vol. 25.

(Continued)

*Primary Examiner* — Michael Fuelling

(57) ABSTRACT

A nuclear imaging system (110) includes a radiation detector (112) having a distance dependent spatial resolution. A reconstructor (124) reconstructs projections acquired by the detector to generate image data. The reconstructor (124) applies a distance dependent projection filter (134) so as to reduce angular dependent resolution variations in the image space data.

23 Claims, 4 Drawing Sheets

OTHER PUBLICATIONS

King, et al., Attenuation, Scatter, and Spatial Resolution Compensation in SPECT, appeared in Emission Tomography: The Fundamentals of PET and SPECT, Sep. 2004, 56 sheets, Academic Press.

Marie, et al., OSEM Reconstruction, Associated with Temporal Fourier and Depth-Dependant Resolution Recovery Filtering, Enhances Results from Sestamibi and 201 T1 16-Intercal Gated SPECT, The Journal of Nuclear Medicine, Nov. 2005, pp. 1789-1795, vol. 46, No. 11.

Ye, et al., Iterative SPECT Reconstruction Using Matched Filtering for Improved Image Quality, 2006 IEEE Nuclear Science Symposium Conference Record, 2006, pp. 2285-2286, M06-433.

Ye, et al., SPECT image quality improvement with Astonish software white paper, Jan. 2006, pp. 1-8.

Philips Medical Systems Nuclear Medicine, Imaging Chain the while picture just got clearer, Jun. 2005, pp. 1-8.

Tom Lewellen, Introduction to Emissions Tomography presentation, Jun. 2006, 9 sheets.

Kohli, V., et al.; Investigation of the Impact of Compensation for the Distance Dependent Resolution on the Uniformity of Maximum Heart Wall Counts and Wall Thickness in Cardiac Perfusion Imaging in SPECT; 1997; IEEE Nuclear Science Symposium; vol. 2; pp. 978-982.

McCarthy, A. W., et al.; Maximum Likelihood SPECT in Clinical Computation Times Using Mesh-Connected Parallel Computers; 1991; IEEE Trans. on Medical Imaging; 10(3)426-436.

Zeng, G. L., et al.; Three-Dimensional Iterative Reconstruction Algorithms with Attenuation and Geometric Point Response Correction; 1991; IEEE Trans. on Nuclear Science; 38(2)693-702.

\* cited by examiner

ISOTROPIC RESOLUTION IMAGE RECONSTRUCTION

CROSS REFERENCE TO RELATED APPLICATIONS

This application claims the benefit of U.S. provisional application Ser. No. 60/910,037 filed Apr. 4, 2007, which is incorporated herein by reference.

The present application relates to image reconstruction. It finds particular application to single photon emission computed tomography (SPECT) and other applications in which it is desirable to compensate for variations in image resolution.

A typical gamma camera includes a gamma radiation detector and a collimator. Collimators conventionally include a plurality of radiation attenuative walls or septa that allow gamma radiation having only a certain angle of incidence to reach the gamma detector. The gamma radiation detector converts received gamma radiation to electrical signals. In a single photon emission computed tomography (SPECT) study, gamma ray projections are acquired from a number of angles with respect to the patient or other object under examination, typically by rotating the detector about, or otherwise varying the relative positions of, the detector and the patient. The projections are then reconstructed to produce volumetric or image space data representative of the distribution of a radionuclide in the object.

The quality of the image data can be influenced by a number of factors, including spatial resolution, noise, scattering, and non-uniform attenuation characteristics of the object. Spatial resolution is influenced by factors such as the characteristics of the gamma detector and the geometry of the collimator. Moreover, the spatial resolution of a gamma detector is typically distance dependent—varying as a function of the distance between the collimator and the object. The detector resolution is ordinarily best at or near the collimator surface and decreases with increasing distance from the collimator.

Iterative reconstruction techniques that model the distance dependent resolution, scatter, and attenuation in the forward projection and/or backprojection steps of the reconstruction process have been developed. In the case of distance dependent detector resolution, the resolution model has considered the distance from the detector surface to the image center. According to such an approach, increasing the number of iterations tends to improve the spatial resolution of the image. Stated another way, the resolution for a given number of iterations is generally improved compared to techniques in which the distance dependent detector resolution is not modeled.

As noted above, however, image quality is also affected by noise. While increasing the number of iterations can ordinarily be expected to improve the accuracy of the image estimate (as well as the spatial resolution in the case of the foregoing distance dependent resolution model), increasing the number of iterations tends to increase image noise. To suppress this noise, a low pass filter has been applied to the projection data generated by the forward projection step of the reconstruction process, and a matching low pass filter has likewise been applied to the measured projection data. The filtered data has been used in the comparison and backprojection steps of the reconstruction process. Another low pass filter has also been applied to the error projection prior the backprojection step. The matched filters have reduced the effects of noise while preserving features that might otherwise have been smoothed past the point of detectability using other filtering techniques, such as pre- and post-reconstruction filtering.

While these techniques have proven to be effective, there remains room for improvement. More particularly, the image resolution at a characteristic feature of the object may not be independent of angle, or isotropic. With this non-isotropic image resolution, a reconstructed point source may appear more like an oval rather than a round dot.

Aspects of the present application address these matters and others.

In accordance with one aspect, a method of reconstructing gamma ray projections acquired during an examination of an object using a detector having a distance dependent resolution includes determining, for a plurality of projections, a distance between the detector and a characteristic feature of the object; varying, as a function of the determined distance, a characteristic of a filter applied to the acquired projections; reconstructing the filtered acquired projections; and generating an image indicative of the reconstructed projections.

According to another aspect of the present invention, an apparatus includes a gamma radiation sensitive detector that acquires projections indicative of radionuclide decays at a plurality of angles with respect to object (106) under examination. A spatial resolution of the detector at a characteristic feature of the object varies as a function of the angle. The apparatus also includes a reconstructor that reconstructs the projections to generate image space data. A spatial resolution of the image space data in the region of the characteristic feature is substantially independent of the angle.

According to another aspect, a computer readable storage medium contains computer readable instructions which, when executed by a processor, cause the processor to carry out a method of iteratively reconstructing projections indicative of radionuclide decays in an object under examination. The method includes filtering projections acquired by a gamma radiation sensitive detector according to a first projection dependent filter function that varies as a function of a distance between the detector and a characteristic feature of the object and using the filtered acquired projections to generate image data indicative of the radionuclide decays.

According to another aspect, a method of reconstructing projections indicative of a distribution of a radionuclide in an object acquired using a detector includes determining, for each of a plurality of projection angles, a distance between the detector and a characteristic feature of the object, reconstructing the projections as a function of the determined distance, and forming an image indicative of the reconstructed projections.

According to another aspect, a single photon emission computed tomography apparatus includes a radiation sensitive detector that acquires projections indicative of radionuclide decays in an object under examination and a reconstructor. A spatial resolution of the detector at a characteristic feature of the object varies as a function of the projection. The reconstructor includes a first filter that filters the acquired projections according to a first filter function and a second filter that filters estimated projections according to a second filter function. The first and second filter functions vary as a function of the spatial resolution.

Still further aspects of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 depicts a single photon emission computed tomography system.

Figure 1:
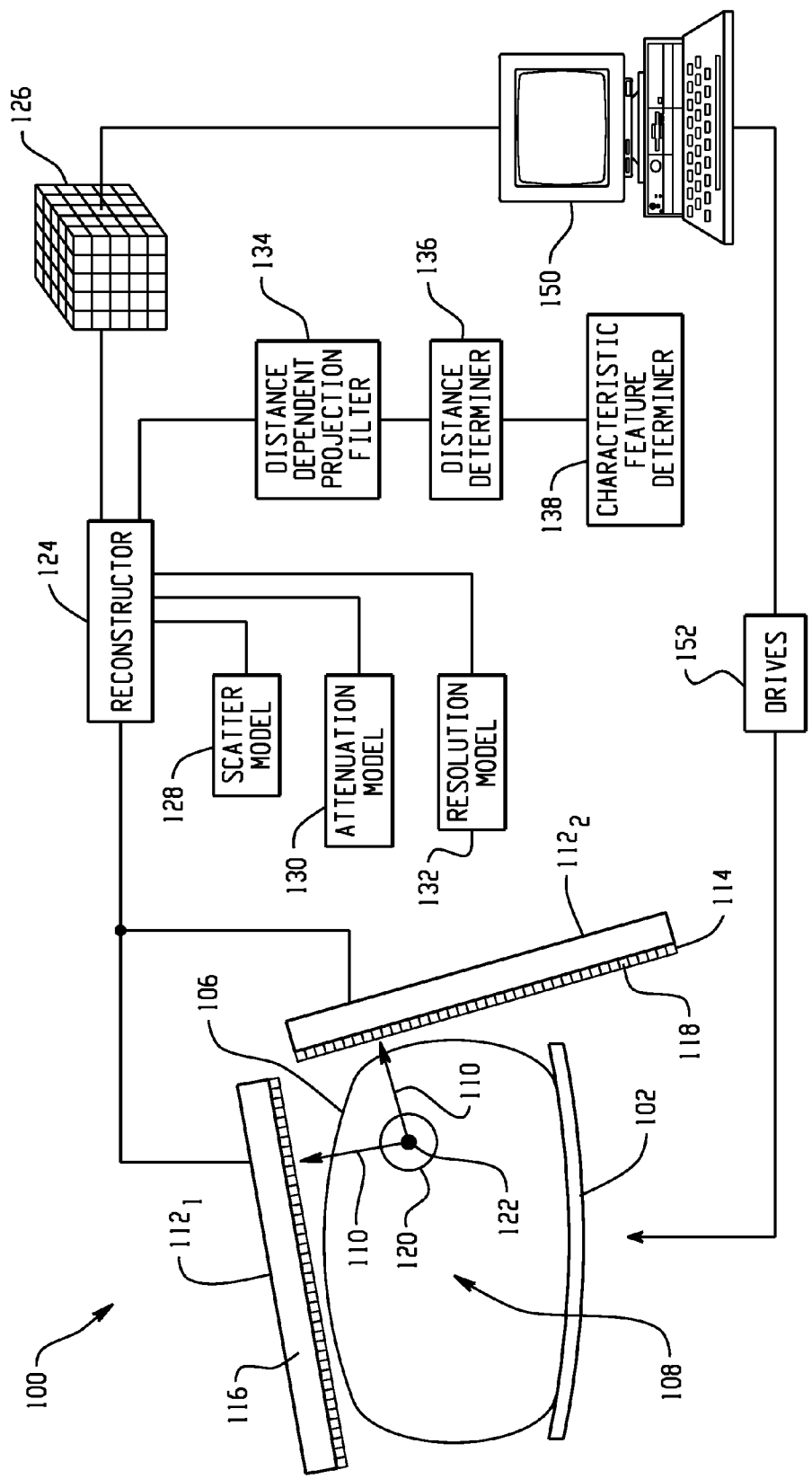

With reference to FIG. 1, a SPECT system 100 includes an object support 102 that supports a patient 106 or other object to be examined in an examination region 108.

A gamma radiation sensitive detector such as detectors $112_1$, $112_2$ acquires projections 110 indicative of radionuclide decays occurring in the examination region 108. The detectors 112 include a collimator 114 and a radiation sensitive detector 116 such as a scintillator and an array photomultiplier tubes (PMTs), semiconductor photodetectors or other light sensitive detectors. Semiconductor or other direct conversion detectors are also contemplated. As will be appreciated by those of ordinary skill in the art, the spatial resolution of the detectors 112 typically decreases as a function of increasing distance from the detector (e.g., as the distance from the face of the collimator 114 increases).

One or more drives 152 varies the relative positions of the detectors 112 and the object, for example by rotating the detectors about the examination region 108 either alone or in coordination with movement of the patient support 102. The drive 152 may include suitable drive(s) for moving the detectors 112 tangentially or radially with respect to the examination region. The relative angular orientation of the detectors $112_1$, $112_2$ may also be adjustable. Various drive 122 and detector 112 configurations are well known to those of ordinary skill in the art and are ordinarily selected based on factors such as performance requirements, size, cost, application, and the like. Note that substantially ring or elliptically shaped detectors 112 may also be implemented.

As illustrated in FIG. 1, two detector heads $112_1$, $112_2$ are disposed in an orthogonal configuration in which the detector heads $112_1$, $112_2$ are disposed relative to each other at an angle in the range of roughly 90° to 102°. Such an orthogonal detector configuration is often used in cardiac imaging as both detectors 112 can be disposed relatively near to the heart 120. As will be appreciated, however, the distance from the detectors 112 and the heart 120 and hence the detector 112 spatial resolution in the region of the heart 120 will vary as the detectors 112 are rotated about the object 106.

Depending on the implementation, the measured projections may be organized as a plurality of spatial, energy, and/or other bins; the projections may also be presented as list mode data.

A characteristic feature determiner 138 determines a location of a characteristic feature 122 of the object. Examples of characteristic features include organs, lesions, or other structures of interest, centers of radionuclide activity, centers of mass, or the like. In the example of cardiac imaging, the characteristic feature may be an approximate center of the heart. In one implementation, the characteristic feature detector 138 determines the location of the characteristic feature 122 in a relatively low resolution reconstruction of the acquired projections, with or without confirmation by the user. In another, the user may be afforded the opportunity to manually identify the characteristic feature 122 in the low resolution image data. The characteristic feature determiner 138 may also operate on image data generated using another imaging modality (e.g., computed tomography CT data in the case of a hybrid SPECT/CT system). Where the location of the characteristic feature 122 can be suitably determined a priori based on known morphological or other characteristics of the object 106, the characteristic feature determiner 138 may be omitted.

A projection dependent distance determiner 136 determines a distance between the detector 112 and the characteristic feature 122 for the various projections. Particularly where the location of the characteristic feature is known a priori, the distance determiner may use a projection angle, detector position, or other variable as a proxy for the distance.

A reconstructor 124 reconstructs the projections to generate image data 126 representative of the detected radiation. As will be described in further detail below, the reconstructor 124 preferably applies a distance dependent resolution model 132 that compensates for the distance-dependent spatial resolution of the detectors 112. Scatter 128, attenuation 130, or other models and/or other corrections may also be applied. As will also be described in further detail below, a distance dependent projection filter 134 is also applied to the projections.

A general purpose computer serves an operator console 150. The console 150 includes a human-readable output device such as a monitor or display and an input device such as a keyboard and mouse. Software resident on the console 150 allows the operator to control the operation of the scanner by establishing desired scan protocols, initiating and terminating scans, viewing and otherwise manipulating the image data 126, and otherwise interacting with the scanner.

Figure 2:
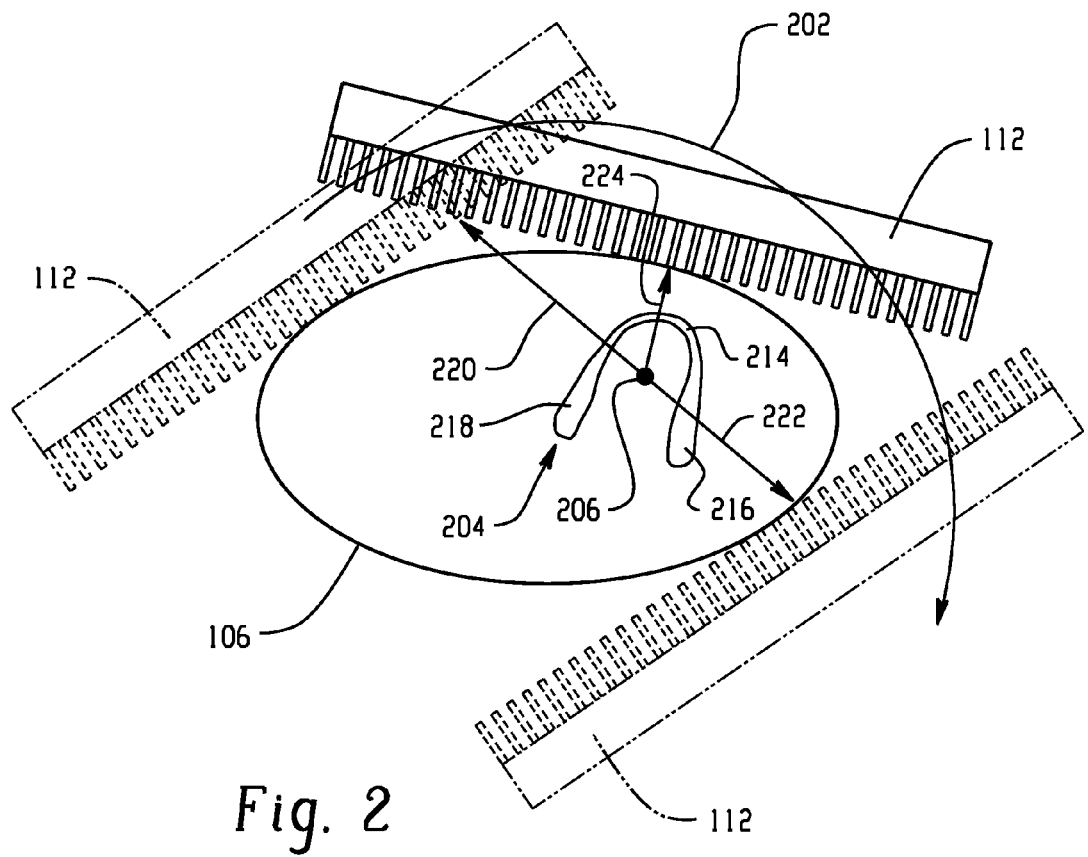
FIG. 2 depicts a detector in a plurality of positions with respect to an object.

Turning now to FIG. 2, the distance between a point in the three-dimensional (3D) object space and a detector 112 typically varies with the relative angular position of the detector 112 and the object 106. As illustrated in FIG. 2 for an example cardiac acquisition, a detector 112 is shown at three (3) angular positions with respect to the object 106: an anterior right oblique or 10 o'clock position, an approximately anterior or 1 o'clock position, and a posterior left oblique or 4 o'clock position. The rotation of the detector 112 relative to the patient 106 is indicated generally by the arrow 202. As can be seen, the distance between the detector 112 and the heart 204 is greater when the detector 112 is in the 10 o'clock position than when the detector 112 is in the 1 o'clock or 4 o'clock positions. Hence, the detector spatial resolution in the region of the heart 204 will vary as a function of the projection angle of the acquired projections. For example, the detector 112 spatial resolution in the region of the heart for projections 220 acquired with the detector in the 10 o'clock position will be lower than detector spatial resolution for projections 222 acquired with the detector 112 in the 4 o'clock position, while the detector 112 will have the best spatial resolution for projections 224 acquired when the detector 112 is in the 1 o'clock position.

Due to the distance dependent resolution of the detector 112, the spatial resolution of the reconstructed images tends to be anisotropic, with the resolution in a given direction strongly influenced by the projections when the face of the detector 112 is nearly parallel to that direction. Thus, in the region of the heart 204, the best resolution is obtained in the 10 o'clock direction (i.e., in a direction roughly perpendicular to line 224). On the other hand, the resolution is typically poorest in the 1 o'clock direction (i.e., in a direction roughly perpendicular to lines 220, 222).

Figure 3:
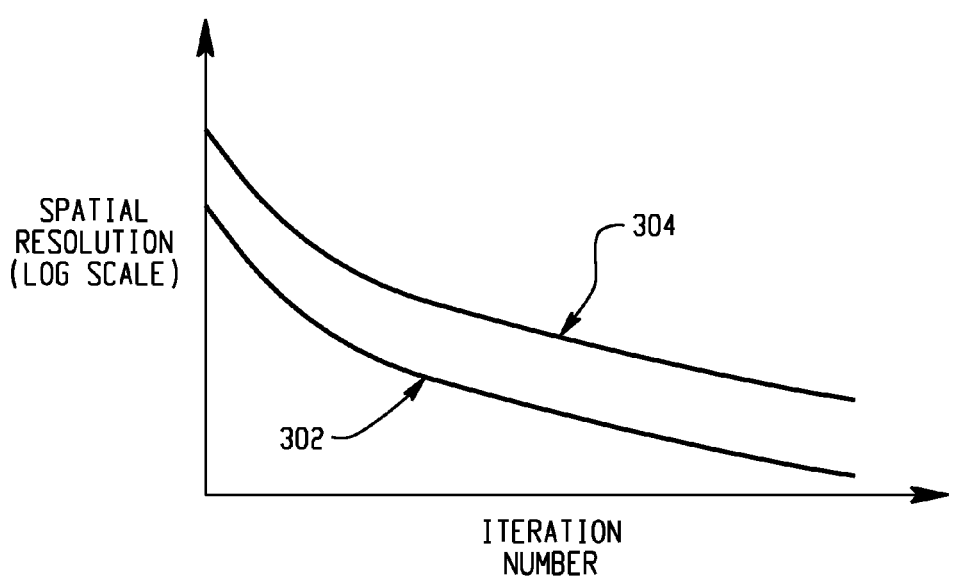
FIG. 3 depicts a resolution as a function of iteration number.

Modeling the depth dependent detector 112 resolution (e.g., by incorporating a blurring model) during the reconstruction can improve the spatial resolution of the resultant image data. Even in the case of an ideal resolution model, however, the reconstructed spatial resolution in a direction with a higher measured resolution recovers faster than in other directions. This is depicted in FIG. 3, in which the abscissa represents the number or iterations, the ordinate represents the log of the spatial resolution, curve 302 represents the resolution in a first direction having a relatively higher spatial resolution, and curve 304 represents the resolution in a second direction having a relatively lower spatial resolution. The variation in the spatial resolution of the reconstructed images can cause the speed of convergence during reconstruction to vary with different direction and location. As a consequence, when a limited number of iterations is used during reconstruction, myocardial perfusion SPECT images can suffer from thinning of the apex 214 and seemingly thicker lateral 216 and septal 218 walls, which is observed as non-uniformity in the myocardium. While increasing the number of iterations improves the spatial resolution in both directions, the resolution in the first direction remains better than the resolution in the second.

Figure 4:
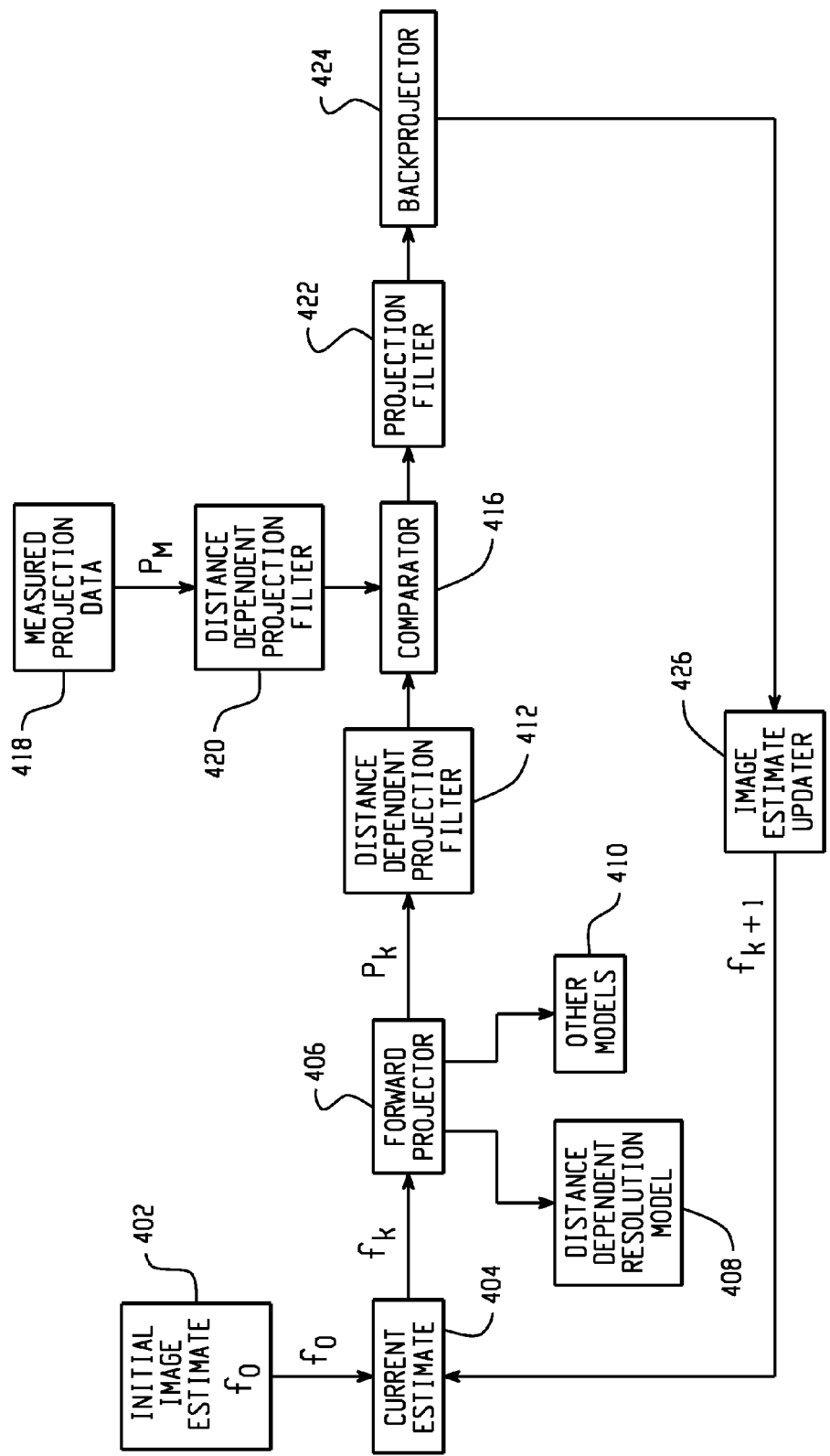
FIG. 4 depicts a reconstructor.

Turning now to FIG. 4, the reconstructor 124 compensates for the differences in convergence speed between the various directions, for example to render reconstructed imaging having a resolution that is substantially isotropic in at least two spatial dimensions. An initial image estimate 402 is used to establish an initial current image estimate 404. A forward projector 406 forward projects the current image estimate 404 to produce image estimate projections $p_k$. The forward projector 406 applies a distance dependent resolution model 408 to compensate for the distance dependent detector resolution using the convolution or other desired technique. The forward projector 406 may also apply other desired models and/or corrections 410 such as those for attenuation and/or scatter.

A first distance dependent filter projection filter 412 filters the projection data $P_k$. The filter function is varied as a function of the distance between the detector 112 and characteristic feature 122 for the various projections. In one implementation, the filter is implemented as a low pass Gaussian filter having a cutoff frequency that is increased as the distance between the detector and the characteristic feature 122 increases. Stated another way, projections acquired at locations where the detector 112 is relatively nearer to the characteristic are filtered relatively more heavily than projection acquired when the detector 112 is relatively more distant. In another implementation, a distance dependent high pass or sharpening filter is applied to projections acquired when the detector is relatively more distant. In another implementation, a distance dependent high pass or sharpening filter is applied to projections acquired when the detector is relatively more distant, while a distance dependent low pass filter is applied to projections acquired when the detector is relatively less distant. Band pass or other filters may also be applied.

A corresponding second distance dependent projection filter 420 filters the projections 418 acquired during the examination of the object 106. The first and second filters preferably have the same distance dependent filter function, although different filter functions may also be implemented.

A comparator 416 compares the filtered estimated projections and the filtered measured projections, for example by determining a ratio or difference therebetween.

To reduce the effects of noise, a low pass projection filter 422 or smoother may also be employed to further filter the compared projections. The projection filter 422 may also apply a distance dependent projection filter analogous to those described above to the compared projections, in which case the filters 412, 420 may be omitted or implemented as distance independent filters.

A backprojector 424 backprojects the (filtered) compared projections. An image updater 426 uses the backprojected data to generate a new image estimate $f_{k+1}$. The updated image estimate is used as the current image estimate $f_k$.

Where the reconstructor 124 carries out the reconstruction according to the ordered subsets expectation maximization (OSEM) algorithm, the process is repeated for each of a plurality of data subsets. Note that the reconstruction may also be carried out according to the maximum likelihood expectation maximization (MLEM) technique or other statistical, iterative or analytical reconstruction algorithms.

In one implementation, the characteristic feature determiner 138 determines the location of the characteristic feature 122 in a relatively low resolution reconstruction of acquired projections, with or without confirmation by the user. In another example, the user may be afforded the opportunity to manually identify the characteristic feature 122 in the low resolution image data. The characteristic feature determiner 138 may also operate on image data generated using another imaging modality (e.g., computed tomography CT data in the case of a hybrid SPECT/CT system). Where the location of the characteristic feature 122 can be suitably determined a priori based on known morphological or other characteristics of the object 106, the characteristic feature determiner 138 may be omitted.

Figure 5:
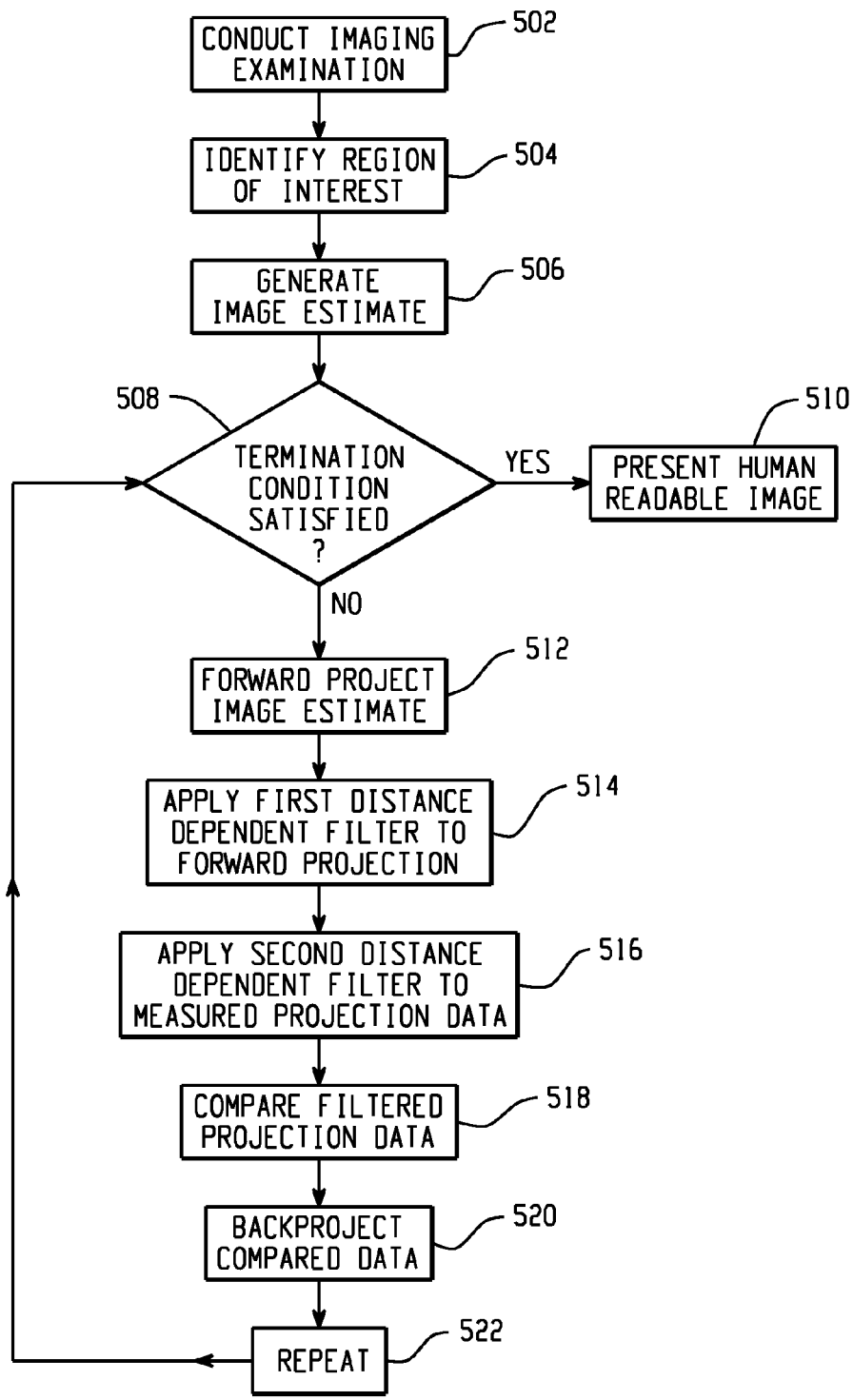
FIG. 5 depicts a method.

Operation will now be described with reference to FIGS. 2 and 5, again for the example case of a cardiac acquisition and an iterative image reconstruction.

An imaging examination of the object 106 is conducted at 502.

The location of a characteristic feature 122 is identified at 504. As illustrated, the characteristic feature is a point of interest 206 such as the approximate center 206 of the heart 204.

An image estimate is generated at 506.

At 508, if a termination condition is satisfied, the image is stored in memory and/or presented in a human readable form at 510.

If not, the image estimate is forward projected at 512 to generate estimated projections. If desired, one or more of distance dependent resolution, attenuation, scatter, or other models may be included in the projection matrix.

At 514, a first distance dependent projection filter is applied to the estimated projections.

At 516, a second distance dependent projection filter is applied to the measured projection data. Note that the second filter may be applied prior to or otherwise at an initial stage of the reconstruction.

At 518, the filtered measured projections and the filtered estimated projections are compared, for example to generate a comparison ratio.

The compared data is backprojected at 520. If desired, one or more of the distance dependent resolution, attenuation, scatter, or other models may be included in the projection matrix, either as an alternative or in addition to the application of the models in connection with the forward projection. As noted above, a filter may be applied to the compared data prior to the backprojection to further reduce the effects of noise.

The process is repeated at 522, with the backprojected data being used to update the image estimate.

Other variations are also possible. For example, a desired distance dependent projection filter 134 function may be applied only to the measured projection data. The filtered measured projection data is then reconstructed using a desired analytical (e.g., filtered backprojection), iterative, or other reconstruction technique. While such an implementation tends to reduce or eliminate geometric distortions that would otherwise be present in the reconstructed image, spatial resolution may be sacrificed relative to the implementation of FIG. 4.

The various components and functions described above may be implemented by way of computer readable instructions contained in computer readable media. When executed by a computer processor(s), the instructions cause the processor(s) to carry out the respective functions.

It will also be appreciated that the reconstruction may, but need not be, performed remote in space and/or time from the image acquisition. For example, some or all of the reconstruction may be performed after the acquisition has been completed and the object 106 is no longer present in the examination region 108. The reconstructor 124 and other relevant components may also be located physically remote from the scanner.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method of reconstructing gamma ray projections acquired during an examination of an object using a detector having a distance dependent resolution, the method comprising:
   for a plurality of projections, determining a distance between the detector and a characteristic feature of the object;
   varying, with a computer processor and as a function of the determined distance, a cut-off frequency of a first filter applied to the acquired projections;
   reconstructing the filtered acquired projections;
   generating an image indicative of the reconstructed projections.

2. The method of claim 1 wherein reconstructing includes
   forward projecting an image estimate to produce estimated projections;
   varying, as a function of the determined distance, a characteristic of a second filter applied to the estimated projections;
   using the filtered acquired projections and the filtered estimated projections to update the image estimate;
   repeating, for each of a predetermined number of the filtered acquired projections, the steps of forward projecting, varying a characteristic of the filter applied to the estimated projections, and using the filtered acquired projections and the filtered estimated projections.

3. The method of claim 2 including varying a characteristic of the filter applied to the acquired projections and a characteristic of the filter applied to the estimated projections so that a spatial resolution of the image estimate at a location of the characteristic feature is substantially isotropic in at least two spatial dimensions.

4. The method of claim 2 wherein the filter applied to the acquired projections includes a low pass filter and the filter applied to the estimated projections includes a low pass filter.

5. The method of claim 2 wherein forward projecting includes modeling the distance dependent resolution of the detector.

6. The method of claim 2 wherein using includes
   comparing the filtered acquired projections and the filtered estimated projections to generate third projections; and
   filtering the third projections according to a filter function that includes a low pass filter.

7. The method of claim 1 wherein reconstructing includes:
   forward projecting an image estimate to produce estimated projections;
   comparing the filtered acquired projections and the estimated projections;
   varying, as a function of the determined distance, a characteristic of a second filter applied to the compared projections;
   using the filtered compared projections to update the image estimate;
   repeating, for each of a predetermined number of the filtered acquired projections, the steps of forward projecting, comparing, varying and using the filtered acquired projections and the filtered estimated projections.

8. The method of claim 1 wherein the characteristic feature includes a region of a heart or a center of activity.

9. The method of claim 1 including filtering projections for which the determined distance is longer than the measured distance with a sharpening filter and projections for which the measured distance is shorter than the determined distance with a smoothing filter.

10. The method of claim 1 including varying a characteristic of the filter applied to the acquired projections so that a spatial resolution of the acquired projections at a location of the characteristic is substantially the same.

11. An apparatus comprising:
    a gamma radiation sensitive detector that acquires projections indicative of radionuclide decays at a plurality of angles with respect to object under examination, wherein a spatial resolution of the detector at a characteristic feature of the object varies as a function of the angle;
    a reconstructor that reconstructs the projections to generate image space data, wherein a spatial resolution of the image space data in the region of the characteristic feature is substantially independent of the angle, wherein the reconstructor includes a first filter that filters the acquired projections according to a cutoff frequency that varies as a function of the detector spatial resolution and a second filter that filters estimated projections according to a second filter function that varies as a function of the detector spatial resolution.

12. The apparatus of claim 11 including a characteristic feature determiner that determines a location of the characteristic feature.

13. The apparatus of claim 11 including a distance determiner that determines a distance between the between the detector and the characteristic feature, and wherein the cutoff frequency varies as a function of the determined distance.

14. The apparatus of claim 11 wherein the second filter functions include a smoothing filter function or a sharpening filter function.

15. The apparatus of claim 11 wherein the reconstructor reconstructs the projections according to a statistical iterative reconstruction technique.

16. The apparatus of claim 11 wherein the reconstructor applies a detector spatial resolution model.

17. The apparatus of claim 11 wherein the detector includes first and second detector heads disposed in an orthogonal relationship.

18. The apparatus of claim 11 wherein a distance between the detector and the characteristic feature varies as a function of a projection angle and further including a distance determiner that uses a morphological characteristic of the object known prior the acquisition of the projections to determine the distance.

19. A non-transitory computer readable storage medium containing computer readable instructions which, when executed by a processor, cause the processor to carry out a method of iteratively reconstructing projections indicative of radionuclide decays in an object under examination, the method comprising:
   filtering projections acquired by a gamma radiation sensitive detector according to a first cut-off frequency that varies as a function of a distance between the detector and a characteristic feature of the object;
   using the filtered acquired projections to generate image data indicative of the radionuclide decays.

20. The non-transitory computer readable storage medium of claim 19, wherein the method includes
   filtering estimated projections according to a second projection dependent filter function that varies as a function of a distance between the detector and the characteristic feature;
   wherein using includes using the filtered estimated projections to generate the image data.

21. The non-transitory computer readable storage medium of claim 19, wherein the method includes
   identifying a center of a heart;
   filtering the acquired projections and the estimated projections so that the spatial resolution of the image data in the region of the heart is substantially isotropic in at least two spatial dimensions.

22. The non-transitory computer readable storage medium of claim 19, wherein the method includes determining, for each of a predetermined number of the filtered acquired projections, a distance dependent spatial resolution of the detector.

23. A method of reconstructing projections indicative of a distribution of a radionuclide in an object acquired using a detector, the method comprising:
   determining, for each of a plurality of projection angles, a distance between the detector and a characteristic feature of the object;
   varying, with a computer processor and as a function of the determined distance, a cut-off frequency of a filter applied to the acquired projections;
   reconstructing the filtered projections as a function of the determined distance;
   forming an image indicative of the reconstructed projections.

* * * * *